US005723656A

United States Patent [19]

Abrams

[11] Patent Number: 5,723,656
[45] Date of Patent: Mar. 3, 1998

[54] PROCESS FOR PREPARING AROMATIC CARBOXYLIC ACIDS WITH EFFICIENT ENERGY RECOVERY

[75] Inventor: Kenneth J. Abrams, Naperville, Ill.

[73] Assignee: Amoco Corporation, Chicago, Ill.

[21] Appl. No.: 603,888

[22] Filed: Feb. 22, 1996

Related U.S. Application Data

[63] Continuation of Ser. No. 323,047, Oct. 14, 1994, abandoned.

[51] Int. Cl.$^6$ ................................................. C07C 51/16
[52] U.S. Cl. ........................... 562/412; 562/409; 562/416
[58] Field of Search .................................... 562/412, 416

[56] References Cited

U.S. PATENT DOCUMENTS

| | | | |
|---|---|---|---|
| 4,471,619 | 9/1984 | Nolley, Jr. | 60/648 |
| 4,914,230 | 4/1990 | Abrams et al. | 562/416 |
| 5,050,375 | 9/1991 | Dickinson | 60/39.12 |
| 5,102,505 | 4/1992 | Sorensen | 203/91 |
| 5,235,117 | 8/1993 | Alagy et al. | 568/837 |
| 5,463,113 | 10/1995 | Yamamoto et al. | 562/414 |

FOREIGN PATENT DOCUMENTS

| | | |
|---|---|---|
| 2187732 | 1/1974 | France . |
| 2303787 | 1/1974 | France . |
| 5213816 | 8/1993 | Japan . |
| 498591A2 | 12/1992 | United Kingdom . |

OTHER PUBLICATIONS

"Energy Conservation at Amoco Chemicals,", by J. Reumers, *Journal A*, vol. 25, no. 3, 1984, pp. 165–67.

*Primary Examiner*—Marianne M. Cintins
*Assistant Examiner*—Dwayne C. Jones
*Attorney, Agent, or Firm*—Thomas E. Nemo; Wallace L. Oliver

[57] ABSTRACT

A process for preparing aromatic carboxylic acids by the exothermic liquid-phase oxidation reaction of an aromatic feedstock compound, wherein energy is efficiently recovered from the exothermic oxidation reaction.

15 Claims, 1 Drawing Sheet

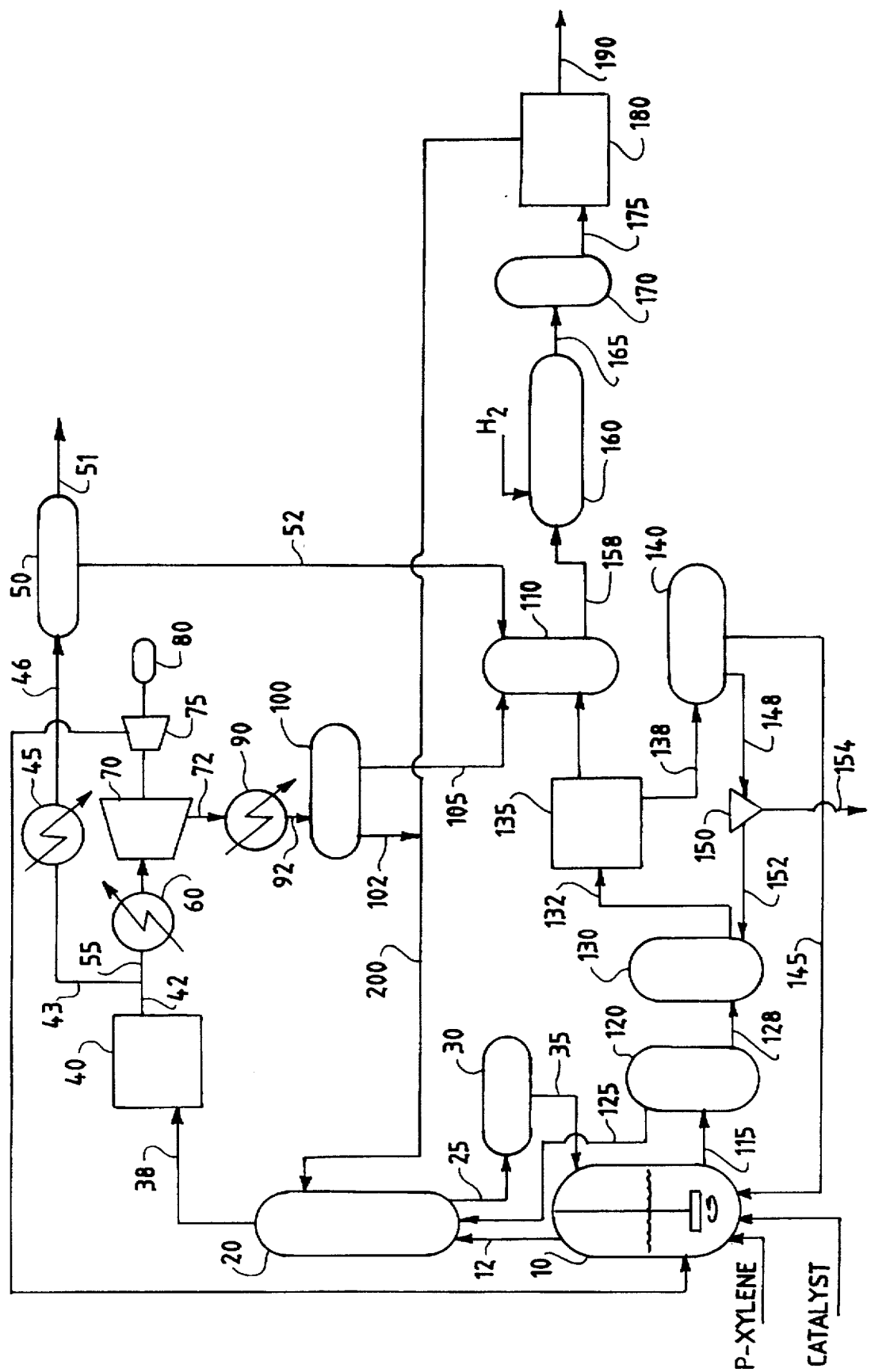

5,723,656

PROCESS FOR PREPARING AROMATIC CARBOXYLIC ACIDS WITH EFFICIENT ENERGY RECOVERY

This is a continuation of application Ser. No. 08/323,047, filed Oct. 14, 1994, now abandoned.

FIELD OF INVENTION

This invention relates to a process for preparing aromatic carboxylic acids by the exothermic, liquid-phase oxidation of an aromatic feedstock compound. More particularly, this invention relates to a process for preparing aromatic carboxylic acids by the exothermic, liquid-phase oxidation of an aromatic feedstock compound wherein the energy produced by the exothermic oxidation is efficiently recovered. This invention also relates to an efficient process for treating waste water produced during the preparation of aromatic carboxylic acids.

BACKGROUND OF THE INVENTION

Aromatic carboxylic acids are useful chemical compounds and are raw materials for a wide variety of manufactured articles. For example, terephthalic acid (TA) is manufactured on a world-wide basis in amounts exceeding 10 billion pounds per year. A single manufacturing plant can produce 100,000 to more than 750,000 metric tons of TA per year. TA is used, for example, to prepare polyethylene terephthalate (PET), a raw material for manufacturing polyester fibers for textile applications and polyester film for packaging and container applications. TA can be produced by the high pressure, exothermic oxidation of a suitable aromatic feedstock compound, such as para xylene, in a liquid-phase reaction using air or other source of molecular oxygen as the oxidant and catalyzed by one or more heavy metal compounds and one or more promoter compounds. Methods for oxidizing para xylene and other aromatic compounds using such liquid-phase oxidations are well known in the art. For example, Saffer in U.S. Pat. No. 2,833,816 discloses a method for oxidizing aromatic feedstock compounds to their corresponding aromatic carboxylic acids. Central to these processes for preparing aromatic carboxylic acids is the use of a liquid-phase reaction employing a low molecular weight carboxylic acid, such as acetic acid, as part of the reaction solvent. A certain amount of water is also present in the oxidation reaction solvent and water is also formed as a result of the oxidation reaction. The oxidation reaction also produces a reaction offgas which generally comprises carbon dioxide, carbon monoxide and, depending on the promoter used, may contain methyl bromide. Additionally, when air is used as the source of molecular oxygen, the reaction offgas contains nitrogen gas and unreacted oxygen. Although various means can be used to control the temperature of the highly exothermic oxidation reaction, it is generally most convenient to remove heat by allowing the solvent to vaporize, i.e. boil, during the oxidation reaction. The vaporized solvent, which is typically a mixture of water and low-molecular weight carboxylic acid, has heretofore been condensed in one or more overhead condenser apparatus and the condensate returned to the reaction mixture. However, since water is also present, at least part of the condensate is usually directed to a separation apparatus, typically a distillation column, to separate the water from the low molecular weight aliphatic acid solvent so that the water concentration in the reactor is maintained at a constant level. The offgases that are not condensed are typically vented or passed through an oxidizer to burn byproducts and form an environmentally acceptable effluent.

The high pressure offgas contains a considerable amount of energy. Although prior art processes have, to an extent, utilized some of the energy contained in the offgas by running the offgas through, for example, an expander or turbine, prior art processes did not fully utilize the energy available in this high pressure offgas. In prior processes, heat removal from the reaction mixture was accomplished by condensing a portion of the reaction overhead vapor to produce moderate pressure steam. The moderate pressure steam, in part, was used to recover energy by a steam turbine, and a part was used to separate water from acetic acid by distillation.

The art, therefore, needs an improved process to manufacture aromatic carboxylic acids wherein the energy generated by the highly exothermic, high pressure oxidation reaction can be economically and efficiently recovered and, in fact, serve as a net generator of energy. The present invention provides such an improved process.

SUMMARY OF THE INVENTION

A continuous process for preparing aromatic carboxylic acids by the exothermic liquid-phase oxidation reaction of an aromatic feedstock compound wherein energy is efficiently recovered from the exothermic liquid-phase oxidation reaction, which process comprises:

a) oxidizing an aromatic feedstock compound to an aromatic carboxylic acid in a liquid-phase reaction mixture comprising water, a low-molecular weight carboxylic acid solvent, a heavy metal oxidation catalyst and a source of molecular oxygen, under reaction conditions which produce a gaseous high pressure overhead stream comprising water, gaseous by-products, and gaseous low-molecular weight carboxylic acid solvent;

b) removing in a high efficiency separation apparatus at least about 95 wt. % of the low-molecular weight carboxylic acid from the overhead stream to form a second high pressure overhead mixture substantially free of low molecular weight carboxylic acid solvent and, comprising water and gaseous byproducts formed during the oxidation reaction; and c) directing the second high pressure overhead mixture to a means for recovering energy from the second high pressure overhead mixture.

In addition to providing for the efficient recovery of energy produced by the exothermic oxidation of the aromatic feedstock compound, the use of a high efficiency separation apparatus, such as a distillation column, provides a means for recycling to the oxidation reactor water typically used for the purification of crude aromatic carboxylic acids. Such water can be recycled as reflux to the distillation column. Any residual aromatic carboxylic acid in the water, as well as oxidation reaction intermediates, are thereby returned to the oxidation reactor and are recovered as useful product. Also, this recycle of the purification water decreases, or even eliminates the need to treat the water in a waste treatment facility. Thus, the load on the waste treatment facility is greatly reduced. Thus, this invention is also a process for preparing aromatic carboxylic acids by the exothermic, liquid-phase oxidation reaction of an aromatic feedstock compound, which process comprises (a) oxidizing an aromatic feedstock compound to an aromatic carboxylic acid in a liquid-phase reaction mixture comprising water, a low molecular weight carboxylic acid solvent, a heavy metal oxidation catalyst, and a source of molecular oxygen under reaction conditions which produce a gaseous overhead stream comprising water, gaseous by-products, and gaseous low-molecular weight carboxylic acid solvent; (b) removing in a high efficiency distillation column at least about 95 weight percent of the low-molecular weight carboxylic acid from the overhead stream to form a second high pressure overhead stream comprising water and gaseous by-products formed during the oxidation reaction; (c) separating the aromatic carboxylic acid formed in step (a) from reaction mother liquor produced during the liquid-phase oxidation reaction mixture to form crude aromatic carboxylic acid; (d) purifying crude aromatic carboxylic acid at an elevated temperature and pressure in a purification solvent comprising water to form a mixture of purified aromatic carboxylic acid and purification mother liquor comprising water; (e) and separating purified aromatic carboxylic acid from purification mother liquor formed in step (d) and recycling at least a portion of the purification mother liquor to the high efficiency distillation column.

This invention is also a reactor apparatus suitable for converting an aromatic feedstock compound to an aromatic carboxylic acid by the liquid phase oxidation of the aromatic feedstock compound in a reaction mixture comprising a low molecular weight aliphatic carboxylic acid and water, and providing for the efficient recovery of energy produced by the oxidation reaction, which reactor apparatus comprises a reactor vessel suitable for conducting the liquid phase oxidation of an aromatic feedstock compound at an elevated temperature, a high efficiency distillation column capable of separating a mixture of acetic acid and water such that vapor exiting the distillation column is less than about 1.0 weight percent acetic acid, and a means for directing vapor produced by the liquid phase oxidation in the reactor to the distillation column.

BRIEF DESCRIPTION OF THE FIGURE

FIG. 1 shows, in schematic form, an embodiment of operating the process of this invention.

DETAILED DESCRIPTION OF THE INVENTION

In the process of this invention an aromatic feedstock compound is oxidized in an exothermic, liquid-phase oxidation reaction mixture to an aromatic carboxylic acid, and the energy generated by this highly exothermic oxidation is efficiently recovered and used, for example, to generate electricity or other forms of useful and transmittable energy.

The aromatic feedstock compound useful in the process of this invention is any aromatic compound that has oxidizable substituents which can be oxidized to a carboxylic acid group. For example, the oxidizable substituent can be an alkyl group such as a methyl, ethyl, or isopropyl group. It can also be a partially oxidized alkyl group such as an alcohol group, aldehyde group or ketone group. The aromatic portion of the aromatic feedstock compound can be a benzene nucleus or it can be bi- or polycyclic, for example a naphthalene nucleus. The number of oxidizable substituents on the aromatic portion of the aromatic feedstock compound can be equal to the number of sites available on the aromatic portion of the aromatic feedstock compound, but is generally fewer, and is preferably 1 to about 4, more preferably 2 or 3. Thus, examples of suitable aromatic feedstock compounds for the process of this invention include toluene, ethylbenzene, o-xylene, meta-xylene, para-xylene, 1-formyl-4-methylbenzene, 1-hydroxymethyl-4-methylbenzene, 1,2,4-trimethylbenzene, 1-formyl-2,4-dimethylbenzene, 1,2,4,5-tetramethylbenzene, alkyl, hydroxymethyl, formyl, and acyl substituted naphthalene compounds such as 2,6- and 2,7-dimethylnaphthalene, 2-acyl-6-methylnaphthalene, 2-formyl-6-methylnaphthalene, 2-methyl-6-ethylnaphthalene, 2,6-diethylnaphthalene, and the like.

Paraxylene, for example, when oxidized produces terephthalic acid, metaxylene produces isophthalic acid and 2,6-dimethylnaphthalene produces 2,6-naphthalenedicarboxylic acid.

As mentioned hereinabove, methods for oxidizing aromatic feedstock to the corresponding aromatic carboxylic acid using a liquid-phase, heavy-metal catalyzed oxidation reaction are well known in the art. For example, Saffer et al. U.S. Pat. No. 2,833,816 discloses such processes. Other processes are disclosed in U.S. Pat. Nos. 3,870,754; 4,933,491; 4,950,786; and 5,292,934. A particularly preferred method for oxidizing 2,6-dimethylnaphthalene to 2,6-naphthalenedicarboxylic acid is disclosed in U.S. Pat. No. 5,183,933. However, in general, suitable heavy metal oxidation catalysts include those metals having an atomic number of about 21 to about 82, inclusive, preferably a mixture of cobalt and manganese. The preferred oxidation solvent is a low molecular weight aliphatic monocarboxylic acid having 2 to about 6 carbon atoms, inclusive, or mixtures thereof with water. Preferably it is acetic acid or mixtures of acetic acid and water. A reaction temperature of about 145° C. to about 235° C. is typical, and the reaction pressure is such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air. For the conversion of paraxylene to terephthalic acid the source of molecular oxygen can vary in molecular oxygen content from that of 10% molecular oxygen, to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the overhead gas-vapor mixture.

The catalyst employed in the oxidation step for producing crude terephthalic acid preferably comprises cobalt, manganese, and bromine components, and can additionally comprise accelerators known in the art. The ratio of cobalt (calculated as elemental cobalt) in the cobalt component of the catalyst-to-p-xylene in the liquid-phase oxidation is suitably in the range of about 0.2 to about 10 milligram atoms (mga) per gram mole of p-xylene. The ratio of manganese (calculated as elemental manganese) in the manganese component of the catalyst-to-cobalt (calculated as elemental cobalt) in the cobalt component of the catalyst in the liquid-phase oxidation is suitably in the range of about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is suitably in the range of about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromine (for example HBr, NaBr, KBr, $NH_4Br$, etc.), or organic bromides which are known to provide bromide ions at the operating temperature of the oxidation (e.g. benzylbromide, mono- and di-bromoacetic acid, bromoacetyl bromide, tetrabromoethane, ethylene-dibromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means.

For the oxidation of paraxylene to terephthalic acid, the minimum pressure at which the oxidation reactor is maintained is typically that pressure which will maintain a substantial liquid phase of the p-xylene and the solvent. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 20 $kg/cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The process conditions described hereinabove for oxidizing paraxylene to terephthalic acid can also be used to oxidize metaxylene to isophthalic acid.

For the oxidation of 2,6-dimethylnaphthalene to 2,6-naphthalenedicarboxylic acid the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1 and the total of cobalt and manganese, calculated as elemental cobalt and elemental manganese is at least about 0.40 weight percent based on the weight of the solvent, and the oxidation reaction temperature is about 185° C. to about 220° C. Acetic acid is the most suitable solvent for oxidation of 2,6-dimethylnaphthalene.

The reactor vessel used for conducting the liquid phase oxidation of the aromatic feedstock compound to the aromatic carboxylic acid is any reactor vessel that is designed to operate at the reaction conditions used for the liquid-phase oxidation reaction. Typically these reactors are constructed of an inert material such as titanium, or are lined with an inert material such as glass or titanium. If the oxidation reaction is conducted at an elevated pressure, the reactor must also be constructed to withstand the pressures used for the oxidation reaction. The reactor can also be equipped with one or more agitators. Generally, the reactor is of a cylindrical design and is positioned in a vertical manner.

As stated hereinabove, the heat generated during the liquid-phase oxidation is dissipated by allowing the reaction solvent to vaporize from the reaction mixture along with the water present in the reaction mixture. Since the temperature at which a liquid boils is related to the pressure; the temperature of the oxidation reaction can be controlled by controlling the reaction pressure. At a reaction pressure of about 7 to about 21 $kg/cm^2$, the temperature of the reaction mixture using acetic acid as the solvent, and the vapor produced therefrom, is about 170° C. to about 210° C. Thus, the high temperature, high pressure vapor generated by the liquid phase oxidation reaction is a considerable source of energy, particularly when one considers the amount of such vapor produced in a large-scale commercial plant producing 200,000 to 750,000 metric tons of aromatic carboxylic acid per year.

In the process of this invention, the vaporized reaction solvent is directed to an apparatus, such as a high efficiency distillation column, that can separate the solvent, typically low molecular weight aliphatic carboxylic acid, from the water produced during the oxidation reaction. For reasons discussed is more detail below, the apparatus used for separating the water from the solvent must be able to make a separation such that at least about 95%, more preferably about 98% and most preferably at least about 99% by weight of the low molecular weight carboxylic acid solvent in the vaporous oxidation reaction stream is removed. Thus, the gaseous stream exiting the separation apparatus has a very low level of reaction solvent and, except for carbon oxides, nitrogen and oxygen gas and any by-products, it is mainly high pressure steam. For example, when the reaction solvent is a low molecular weight carboxylic acid such as acetic acid, the vapor entering the separation apparatus comprises a mixture of acetic acid and water wherein the ratio of acetic acid to water, by weight, is about 20:1 to about 3:1, and the vapor exiting the separation apparatus is generally less than about 0.5 weight percent acetic acid, more preferably less than about 0.1 weight percent acetic acid and most preferably less than about 0.05 weight percent acetic acid.

Although the apparatus used to conduct this separation can be any apparatus that can separate water from the reaction solvent the preferred apparatus or means for conducting such a separation is a distillation column, preferably a high-efficiency distillation column. Any high efficiency distillation column can be used; however, preferable distillation columns are those containing a high efficiency packing such as Koch Flexipac and the like or containing sieve, valve or bubble cap trays. Preferably, the distillation column has at least about 30 theoretical plates, more preferably, at least about 50 theoretical plates. The distillation column must be able to make a separation such that at least 95%, more preferably about 98% and most preferably at least about 99% by weight of the low molecular weight carboxylic acid solvent in the vaporous overhead oxidation reaction stream is removed. As stated above, in these overhead streams, the ratio of low molecular weight monocarboxylic acid, such as acetic acid, to water, by weight, is typically about 20:1 to about 2:1.

Preferably, the separation apparatus is designed to make the separation of the reaction solvent from water at elevated pressure. The separation apparatus is preferably operated at a pressure equal to or slightly below the pressure of the liquid phase oxidation reaction.

Any means can be used to direct the vapor produced by the liquid phase oxidation reaction to the separation apparatus. For example, piping or other suitable conduit can be used. Additionally, the separation apparatus, such as a distillation column, can be directly connected to the reactor vessel used to conduct the liquid phase oxidation reaction.

Thus, the vapor produced by the liquid phase oxidation reaction, along with any byproduct gases formed as a result of the oxidation, any carbon oxides formed during the oxidation and, if air is used as the source of molecular oxygen, nitrogen gas, are passed through the separation apparatus to remove most of the reaction solvent. The gas exiting the separation apparatus therefore generally comprises water (steam), carbon oxides, nitrogen gas, any unconsumed molecular oxygen, and oxidation reaction byproducts such as methyl bromide. Significantly, the gas exiting the separation apparatus is still at a high pressure and is, therefore, a valuable source of energy. While this offgas from the separation apparatus can be sent to a means for recovering energy, e.g. an expander, it is preferable to first remove corrosive and/or combustible byproduct materials from the high pressure offgas before it is directed to an expander or other means for energy recovery. While any means for removing combustible materials from the offgas is suitable, for example, a thermal oxidizer, a preferred method is to use a catalytic oxidation apparatus wherein the offgas is contacted with a suitable catalytic material at high temperature and high pressure in the presence of air or other source of molecular oxygen, and the corrosive and combustible byproduct materials in the offgas are catalytically oxidized to environmentally compatible materials. Such a catalytic oxidation unit can reduce or eliminate through oxidation, any residual oxidation reaction solvent present in the offgas, and it can oxidize a byproduct such as methyl bromide. However, in the method of this invention, the separation apparatus used removes most of the reaction solvent from the reaction offgas. Thus, the offgas entering the offgas catalytic oxidation unit has a low level of reaction solvent so the load on the catalytic oxidation unit is small. Otherwise, a high load of reaction solvent on the offgas catalytic oxidation unit would result in an excessively large temperature rise in the catalytic oxidation unit. Furthermore, the combustion of the reaction solvent would be a great economic loss since it is desirable to conserve and recycle as much of the oxidation reaction solvent as possible. Generally, the effluent from the catalytic oxidation unit is directed to a scrubber to remove any acidic, inorganic materials such as bromine and hydrogen bromide. Bromine and hydrogen bromide would be formed by the catalytic oxidation of methyl bromide. Oxidation catalysts for such offgas oxidation are available, for example, from Engelhard Corp. or AlliedSignal Inc.

The gaseous, high pressure effluent from the catalytic oxidation unit and scrubber is preferably directed to a pre-heater to elevate the temperature of the offgas and thereby convert any condensed water that may be present to steam. The dry, high pressure gas stream exiting the pre-heater is directed to an expander or other means for recovering energy from the high pressure gas stream.

The means for recovering energy from the high pressure offgas, e.g. an expander, is suitably connected to an electric generator and/or to other equipment requiring mechanical work such as a compressor. The electrical energy produced by a generator can be used to power the equipment used in the plant for manufacturing the aromatic carboxylic acid, for example, it can be used to operate compressors for adding air to the liquid phase oxidation reaction, and any excess electrical energy can be transmitted to a local electric power utility. For the production of terephthalic acid from paraxylene feedstock, the amount energy recovered in the process of this invention is at least about 0.3 and more preferably at least about 0.35 kilowatt hours per pound of terephthalic acid produced.

After exiting the expander, the offgas is condensed and the resulting water is useful in other processes within the manufacturing plant. This water is of relatively high purity containing only a small amount of dissolved gasses. For example, the condensed water can be used as a reflux for a distillation column used as a high efficiency separation apparatus. The water produced by the condensation of the offgas can also be used as the solvent for a purification step where the crude aromatic carboxylic acid is treated to from a purified aromatic carboxylic acid. Thus, the water formed by the condensation from the reaction offgas can be used as a recrystallization solvent or as a solvent for conducting one or more chemical and/or physical treatments for the crude aromatic carboxylic acid. One such purification process comprises contacting an aqueous solution or slurry of the crude aromatic carboxylic acid with hydrogen at an elevated temperature and pressure in the presence of a hydrogenation catalyst. Such a process is disclosed in U.S. Pat. No. 3,584,039 to Meyer. Using the purification of terephthalic acid as an example, this purification procedure is conducted at an elevated temperature and pressure in a fixed catalyst bed. Both down-flow and up-flow reactors can be used. The crude terephthalic acid to be purified is dissolved in water or a mixture of water and some other polar solvent such as a $C_1$–$C_4$ aliphatic carboxylic acid.

The reactor, and thus the terephthalic acid solution temperature during purification, can be in the range of about 100° C. to about 350° C. Preferably the temperatures are in the range of about 275° C. to about 300° C.

Reactor pressure conditions primarily depend upon the temperature at which the purification process is carried out. Inasmuch as the temperatures at which practical amounts of the impure terephthalic acid may be dissolved are substantially above the normal boiling point of the solvent, the process pressures are necessarily considerably above atmospheric pressure to maintain the aqueous solutions in liquid phase. In general, the reactor pressure during hydrogenation can be in the range of about 200 to about 1500 pounds per square inch gauge (psig), and usually is in the range of about 900 psig to about 1,200 psig. The hydrogen partial pressure is typically in the range of about 30 psig to about 200 psig.

The catalyst used for this purification step comprises one or more active hydrogenation metals such as ruthenium, rhodium, palladium or platinum on a suitable support such as carbon or titania. A suitable support is an active carbon, usually derived from coconut charcoal in the form of granules having a surface area of 600 $m^2$/g to 1500 $m^2$/g. The loading of metal on the carrier is suitably about 0.01 weight percent to about 2 weight percent. Suitable materials for preparing purified aromatic carboxylic acids from crude aromatic carboxylic acids are disclosed in U.S. Pat. No. 5,256,817 to Sikkenga et al., and in U.S. patent application Ser. No. 029,037, filed on Mar. 10, 1993, to Schroeder et al.

After passing through the reactor for purifying the aromatic carboxylic acid, the solution of aromatic acid in aqueous solvent is cooled to precipitate the purified aromatic carboxylic acid. The temperature to which the solution is cooled is such that most of the purified aromatic carboxylic acid crystallizes. The crystallized purified aromatic carboxylic acid is separated from the aqueous mother liquor using a suitable solid-liquid separation device such as a centrifuge or filter. The cake of purified aromatic carboxylic acid can be washed with pure water, dried and sent to storage or for packaging and shipment.

The aqueous mother liquor separated by the centrifuge or filter contains a number of impurities, reaction intermediates and also contains suspended and dissolved aromatic carboxylic acid. In prior processes, this stream would be sent to a waste treatment facility. However, in the process of this invention, a major portion of this mother liquor can be diverted to the separation apparatus used for separating the oxidation reaction solvent from the water produced during the oxidation reaction. Thus, the impurities, reaction intermediates and aromatic carboxylic acid product are returned to the oxidation reaction mixture. Impurities are oxidized further, intermediates are converted to useful product, and aromatic carboxylic acid is recycled for recovery. Such a recycle of the mother liquor from the hydrogenation reaction is particularly useful when the separation apparatus used for separating water from the oxidation reaction solvent is a distillation column. The recycled aqueous mother liquor returned to the distillation column not only serves as reflux for the column, but also serves as an effective method for adding the mother liquor from the purification process to the oxidation reaction mixture. Thus the process of this invention provides for the elimination of a major waste product stream, a stream that would otherwise be sent to a waste treatment facility. Prior to recycling the mother liquor stream to the distillation column it can be treated to remove any suspended matter, if present. For example, it can be subjected to filtration or centrifugation, or it can be passed through a hydroclone to remove suspended matter. Prior to such treatment to remove suspended matter, the mother liquor can be treated, for example, by cooling, to remove dissolved compounds that might otherwise foul the distillation column.

DETAILED DESCRIPTION OF THE FIGURE

FIG. 1 shows in schematic form a preferred embodiment for operating the process of this invention. In agitated oxidation reactor 10 para-xylene is reacted with air in the presence of acetic acid, and water as the oxidation solvent, cobalt and manganese oxidation metals and one or more bromine compounds such as hydrogen bromide as an oxidation promoter. The oxidation reaction is conducted at a temperature of about 170° C. to about 210° C., and at a pressure of about 7 to about 21 kg/cm². The heat generated by the exothermic oxidation reaction causes the reactor solvent to boil. The vaporized solvent along with gaseous byproducts, carbon oxides, nitrogen from the air charged to the oxidation reaction, and unreacted oxygen pass through pipe 12 and into high pressure distillation column 20 having about 45 theoretical plates. In the distillation tower, the acetic acid solvent is separated from the reaction overhead or offgas. The distillation column is constructed and operated such that at least 99% of the acetic acid is removed from the overhead gas. The acetic acid solvent from the bottom of the distillation column is directed to surge drum 30 through pipe 25. From surge drum 30 the acetic acid solvent, which may contain some water, is returned to reactor 10 through pipe 35. The amount of solvent returned is controlled so that the proper amount of reaction solvent is maintained in the oxidation reactor.

The reaction overhead or offgas exiting the top of distillation tower 20 through pipe 38 contains less than about 0.1% by weight acetic acid, and is primarily water (steam), but also contains nitrogen, carbon oxides, unreacted oxygen and gaseous oxidation byproducts such as methyl bromide. Offgas from pipe 38 is treated in a catalytic oxidation unit 40 where byproducts such as methyl bromide and any residual acetic acid in the offgas are catalytically oxidized. Catalytic oxidation unit 40 is also equipped with an aqueous scrubber to remove any bromine in the offgas exiting the catalytic oxidation unit. If acetic acid was not efficiently removed from the oxidation reaction overhead, it would be oxidized in the catalytic oxidation unit resulting in an economic loss. Offgas exiting the catalytic oxidation unit 40 is directed to pipe 42. A portion of the offgas from pipe 42 is directed to pipe 43 and then to condenser 45 where water is condensed from the offgas. The cooled offgas is directed to knock-out drum 50 through pipe 46. The water depleted gas exits the process through pipe 51. The water from knock-out drum 50 is directed to PTA slurry vessel 110.

The offgas, which is primarily water, from pipe 42 is directed to pre-heater 60 through pipe 55. In pre-heater 60, the offgas is heated to a temperature of about 200° C. to about 235° C. and sufficient to prevent the condensation of the acetic acid depleted reactor offgas in the expander 70. Pre-heated reactor offgas enters expander 70 through pipe 65. Expander 70, which recovers energy from the reactor offgas, drives compressor 75 which delivers compressed air to oxidation reactor 10 through pipe 76. Expander 75 also drives electric generator 80 which supplies electric power for use within the TA manufacturing plant and to the local power utility.

The expanded reactor offgas exits expander 70 through pipe 72 and enters condenser 90 where the water in the expanded offgas is condensed. The condensed water from condenser 90 is directed to reflux drum 100 through pipe 92. Water from drum 100 is directed to high pressure distillation column 20 through pipes 102 and 200. Such water returned to the column serves as reflux for the column. Water from drum 100 is also directed to PTA slurry vessel 110 through pipe 105.

A reaction mixture slurry comprising crude terephthalic acid, water, acetic acid, catalyst metals, oxidation reaction intermediates and by-products exits oxidation reactor 10 through pipe 115 and is directed to vessel 120 where the temperature of the oxidation reaction mixture is reduced to crystallize dissolved terephthalic acid. Vessel 120 is optionally equipped with an air sparger to continue the oxidation reaction. Overhead gasses from vessel 120 are directed to high pressure distillation column 20 having about 45 theoretical plates, through pipe 125. Oxidation reaction slurry from vessel 120 is directed to vessel 130 through pipe 128 wherein additional cooling and crystallization of terephthalic acid occurs. Oxidation reaction mixture slurry from vessel 130 enters separation apparatus 135 through pipe 132. Separation apparatus 135 is typically one or more centrifuges or filters. In separation apparatus 135, crude terephthalic acid is separated from the oxidation reaction mother liquor. Oxidation reaction mother liquor exits separation apparatus 135 through pipe 138 and enters mother liquor drum 140. A major portion of the mother liquor containing catalyst and acetic acid is recycled to oxidation reactor 10 through line 145. The other portion of the mother liquor is sent to stripper 150 through pipe 148 where acetic acid is removed and directed to vessel 130 through line 152. Bottoms from stripper 150 are sent to waste through pipe 154.

A slurry of crude terephthalic acid and water from PTA slurry drum 110 is directed to hydrogenation reactor 160 through pipe 158. In reactor 160, the crude terephthalic acid dissolved in water is treated with hydrogen at an elevated temperature, for example, about 260° C. to about 290° C., and elevated pressure to purify the crude terephthalic acid by, for example, reducing the levels of 4-carboxybenzaldehyde. The reaction mixture from hydrogenation reactor 160 enters crystallization vessel 170 through pipe 165. The slurry of purified terephthalic acid and water formed in vessel 170 is directed to separation apparatus 180 through pipe 175. Purified terephthalic acid exits separation apparatus 180 through pipe 190. Separation apparatus 180 is generally a centrifuge or a rotary vacuum filter. Mother liquor from separation apparatus 180 which comprises water, dissolved and suspended purified terephthalic acid, and various intermediate and by-product compounds, is recycled to the top of high pressure distillation column 20 through pipe 200. The return of the mother liquor from separation apparatus 180 to high pressure distillation column 20 allows for the recycle of the intermediates and by-products in the mother liquor to the oxidation reactor where they are either oxidized or converted to terephthalic acid, it also provides for the recycle of valuable terephthalic acid which would otherwise be sent to waste treatment, or which would require costly procedures for its recovery, and it eliminates treating large volumes of waste water in waste treatment facilities.

Having described the invention, that which is claimed is:

1. A continuous process for preparing aromatic carboxylic acids by the exothermic liquid-phase oxidation reaction of an aromatic feedstock compound wherein energy is efficiently recovered from the exothermic liquid-phase oxidation reaction, which process comprises:

(a) oxidizing an aromatic feedstock compound to an aromatic carboxylic acid in a liquid-phase reaction mixture comprising water, a low-molecular weight monocarboxylic acid solvent, a heavy metal oxidation catalyst and a source of molecular oxygen, under reaction conditions which produce a gaseous high pressure overhead stream comprising water, gaseous by-products, and gaseous low-molecular weight monocarboxylic acid solvent;

(b) removing in a high efficiency separation apparatus at least about 95 wt. % of the low-molecular weight monocarboxylic acid solvent from the gaseous high pressure overhead stream from the liquid-phase oxidation reaction to form a second gaseous high pressure overhead stream comprising water and gaseous by-products formed during the oxidation reaction; and (c) directing the second gaseous high pressure overhead stream to a means for recovering energy from the second high pressure overhead stream.

2. The process of claim 1 wherein the high efficiency separation apparatus is a high efficiency distillation column.

3. The process of claim 2 wherein the high efficiency distillation column has at least about 30 theoretical plates.

4. The process of claim 1 wherein the means for recovering energy from the second high pressure overhead mixture is an expander.

5. The process of claim 4 wherein the expander is connected to an electric generator.

6. The process of claim 1 wherein the aromatic feedstock compound is para-xylene and the aromatic carboxylic acid is terephthalic acid.

7. The process of claim 6 wherein the low-molecular weight monocarboxylic acid solvent is acetic acid.

8. The process of claim 1 wherein water in the high pressure overhead stream is used for the purification of the aromatic carboxylic acid.

9. A process for preparing aromatic carboxylic acids by the exothemic, liquid-phase oxidation reaction of an aromatic feedstock compound, which process comprises:

(a) oxidizing an aromatic feedstock compound to an aromatic carboxylic acid in a liquid-phase reaction mixture comprising water, a low molecular weight monocarboxylic acid solvent, a heavy metal oxidation catalyst, and a source of molecular oxygen, under reaction conditions which produce a gaseous overhead stream comprising water, gaseous by-products, and gaseous low-molecular weight monocarboxylic acid solvent;

(b) removing in a high efficiency distillation column at least about 95 weight percent of the low-molecular weight monocarboxylic acid from the overhead stream from the liquid-phase oxidation reaction to form a second high pressure overhead stream comprising water and gaseous by-products formed during the oxidation reaction;

(c) separating the aromatic carboxylic acid formed in step (a) from reaction mother liquor produced during the liquid phase oxidation reaction mixture to form crude aromatic carboxylic acid;

(d) purifying crude aromatic carboxylic acid at an elevated temperature and pressure in a purification solvent comprising water to form a mixture of purified aromatic carboxylic acid and purification mother liquor comprising water;

(e) separating purified aromatic carboxylic acid from purification mother liquor formed in step (d) and recycling at least a portion of the purification mother liquor to the high efficiency distillation column.

10. The process of claim 9 wherein the aromatic feedstock compound is para-xylene and the aromatic carboxylic acid is terephthalic acid.

11. The process of claim 10 wherein the low molecular weight monocarboxylic acid solvent is acetic acid.

12. The process of claim 9 wherein the high efficiency distillation column has at least about 30 theoretical plates.

13. The process of claim 9 wherein the purification solvent is water.

14. The process of claim 9 wherein in step (d) hydrogen is used to purify the crude aromatic carboxylic acid.

15. The process of claim 9 wherein at least most of the purification mother liquor is recycled to the high efficiency distillation column.

* * * * *